United States Patent
Nguyen (10) Patent No.: US 9,943,322 B2
(45) Date of Patent: Apr. 17, 2018

(54) MEDICAL RETRIEVAL DEVICES AND METHODS

(71) Applicant: Boston Scientific Scimed, Inc., Maple Grove, MN (US)

(72) Inventor: Man Minh Nguyen, Harvard, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 377 days.

(21) Appl. No.: 14/790,632

(22) Filed: Jul. 2, 2015

(65) Prior Publication Data

US 2016/0008015 A1 Jan. 14, 2016

Related U.S. Application Data

(60) Provisional application No. 62/022,320, filed on Jul. 9, 2014.

(51) Int. Cl.
*A61B 17/22* (2006.01)
*A61B 17/221* (2006.01)
*A61B 17/00* (2006.01)

(52) U.S. Cl.
CPC .. *A61B 17/221* (2013.01); *A61B 2017/00358* (2013.01); *A61B 2017/2212* (2013.01); *A61B 2017/2215* (2013.01)

(58) Field of Classification Search
CPC .......... A61B 17/221; A61B 2017/2212; A61B 17/22031; A61B 2017/22035; A61B 2017/00358
See application file for complete search history.

(56) References Cited

U.S. PATENT DOCUMENTS

| 5,522,819 | A | 6/1996 | Graves et al. |
| 6,174,318 | B1 | 1/2001 | Bates et al. |
| 6,368,328 | B1 | 4/2002 | Chu et al. |
| 6,652,537 | B2 | 11/2003 | Mercereau et al. |
| 7,753,919 | B2* | 7/2010 | Kanamaru ............. A61B 17/22 606/114 |
| 8,512,351 | B2 | 8/2013 | Teague |
| 8,597,303 | B2 | 12/2013 | Hammack et al. |
| 2004/0138677 | A1 | 7/2004 | Little et al. |
| 2006/0293697 | A1* | 12/2006 | Nakao ................. A61B 17/221 606/127 |
| 2011/0213381 | A1 | 9/2011 | Leslie et al. |

(Continued)

*Primary Examiner* — Jonathan Miles
(74) *Attorney, Agent, or Firm* — Bookoff McAndrews, PLLC (57) ABSTRACT

A device may include a distal assembly including a first plurality of legs, a second plurality of legs, and a distal tip, and further include a first driver and a second driver, a proximal end of at least one leg of the first plurality of legs may be coupled to the first driver, and a proximal end of at least one leg of the second plurality of legs may be coupled to the second driver. The medical device may include a first longitudinally extending hollow member movably positioned along the first driver and a second longitudinally extending hollow member movably positioned along the second driver. Movement of the first longitudinally extending hollow member relative to the first driver may converge legs of the first plurality of legs, and movement of the second longitudinally extending hollow member relative to the second driver may converge legs of the second plurality of legs.

18 Claims, 3 Drawing Sheets

(56) References Cited

U.S. PATENT DOCUMENTS

2013/0131688 A1   5/2013  Schwartz
2015/0100117 A1*  4/2015  Bortlein ........... A61B 17/00234
                                                       623/2.11

* cited by examiner

MEDICAL RETRIEVAL DEVICES AND METHODS

CROSS REFERENCE TO RELATED APPLICATIONS

This application claims the benefit of U.S. Provisional Application No. 62/022,320, filed Jul. 9, 2014, the disclosure of which is incorporated herein by reference in its entirety.

TECHNICAL FIELD

The disclosure generally relates to medical retrieval devices such as, for example, baskets, for retrieving material in a body of a patient. More particularly, the disclosure generally relates to medical retrieval baskets with release mechanisms and methods of use.

BACKGROUND

Medical retrieval devices are often utilized for removing organic material (e.g., blood clots, tissue, and biological concretions such as urinary, biliary, and pancreatic stones) and inorganic material (e.g., components of a medical device or other foreign matter), which may obstruct or otherwise be present within a patient's body cavities. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy (PNCL) procedure. Other procedures may include endoscopic retrograde cholangiopancreatography (ERCP) which is a procedure for treating the bile and pancreatic ducts of a patient. Further, lithotripsy and ureteroscopy, for example, are used to treat urinary calculi (e.g., kidney stones) in the ureter of a patient.

One problem commonly associated with medical retrieval baskets occurs where the stone or other material is too large to be removed intact from the body tract after it has been captured within the medical retrieval basket. In such cases, medical professionals may attempt to dislodge the stone or other material from the basket. If the stone or material cannot be removed from the basket in this manner, however, a medical professional often must use an emergency rescue handle to attempt to break the stone in the basket. If the stone or material doesn't break, the basket tends to break along its drive wire. The patient may then need to undergo surgery to remove the broken basket.

SUMMARY

Embodiments of the present disclosure relate to, among other things, medical retrieval devices and related methods of use.

Each of the embodiments disclosed herein may include one or more of the features described in connection with any of the other disclosed embodiments.

In one embodiment, a medical device may comprise a distal assembly including a first plurality of legs, a second plurality of legs, and a distal tip. The medical device may further include a first driver and a second driver, wherein a proximal end of at least one leg of the first plurality of legs may be coupled to the first driver, and a proximal end of at least one leg of the second plurality of legs may be coupled to the second driver. In addition, the medical device may include a first longitudinally extending hollow member movably positioned along the first driver and a second longitudinally extending hollow member movably positioned along the second driver. Movement of the first longitudinally extending hollow member relative to the first driver may converge legs of the first plurality of legs, and movement of the second longitudinally extending hollow member relative to the second driver may converge legs of the second plurality of legs.

Embodiments of the medical device may include one or more of the following features: the distal tip may be atraumatic; each of the first plurality of legs and the second plurality of legs may include a proximal portion and a distal portion, wherein the distal portion may include more legs than the proximal portion; the proximal portion may comprise four legs and the distal portion may comprise eight legs; the proximal portion of the first plurality of legs may comprise a different number of legs than the proximal portion of the second plurality of legs; the first plurality of legs and the second plurality of legs may comprise at least one or more of synthetic plastic, stainless steel, and superelastic metallic alloys; the first plurality of legs and the second plurality of legs may be cut from a tube; each of the first longitudinally extending hollow member and the second longitudinally extending hollow member may be independently movable; each of the first longitudinally extending hollow member and the second longitudinally extending hollow member may be configured to slide over a corresponding one of the first plurality of legs and the second plurality of legs; wherein each of the first longitudinally extending hollow member and the second longitudinally extending hollow member may comprise a coil or a hypotube; each of the first longitudinally extending hollow member and the second longitudinally extending hollow member may comprise stainless steel; each of the first longitudinally extending hollow member and the second longitudinally extending hollow member may include a lubricious coating; a handle coupled to a sheath, wherein the handle may include an actuator configured to reciprocally move the first plurality of legs and the second plurality of legs from a position within the sheath to a position extending distally of the sheath; the actuator may comprise at least one of a sliding mechanism, a rotating mechanism, or a pushing mechanism; and a first hollow member actuator and a second hollow member actuator may be configured to reciprocally move the first longitudinally extending hollow member and the second longitudinally extending hollow member relative to the first driver and to the second driver, respectively.

In another embodiment, a method may include delivering a medical device to an area within a patient. The medical device may comprise a first driver, a second driver, and a distal assembly. The distal assembly may be configured to transition between a first retracted configuration within a sheath and a second deployed configuration extending distally of the sheath. The method may also include moving the distal assembly to the deployed configuration and capturing an object of interest within the distal assembly. The distal assembly may include a first plurality of legs, a second plurality of legs, and a distal tip. A proximal end of at least one leg of the first plurality of legs may be coupled to the first driver, and a proximal end of at least one leg of the second plurality of legs may be coupled to the second driver. The method may further include extending a first longitudinally extending hollow member relative to the first driver and converging legs of the first plurality of legs, and extending a second longitudinally extending hollow member relative to the second driver and converging legs of the second plurality of legs.

Embodiments of the method may include one or more of the following features: releasing the object of interest; retracting the first longitudinally extending hollow member relative to the first driver and retracting the second longitudinally extending hollow member relative to the second driver; wherein extending the first longitudinally extending hollow member relative to the first driver and the second longitudinally extending hollow member relative to the second driver comprises extending the first longitudinally extending hollow member independently of the second longitudinally extending hollow member; actuating a first hollow member actuator to extend the first longitudinally extending hollow member and actuating a second hollow member actuator to extend the second longitudinally extending hollow member; and wherein each of the first longitudinally extending hollow member and second longitudinally extending hollow member may comprise a coil or a hypotube.

In another embodiment, a method may comprise delivering a medical device to an area within a patient. The medical device may comprise a first driver, a second driver, and a distal assembly. The distal assembly may be configured to transition between a first retracted configuration within a sheath and a second deployed configuration extending distally of the sheath. The method may also include moving the distal assembly to the deployed configuration and capturing an object of interest within the distal assembly. The distal assembly may include a first plurality of legs, a second plurality of legs, and a distal tip. A proximal end of at least one leg of the first plurality of legs may be coupled to the first driver and a proximal end of at least one leg of the second plurality of legs may be coupled to the second driver. The method may also include extending a first longitudinally extending hollow member relative to the first driver to converge legs of the first plurality of legs. The first longitudinally extending hollow member may comprise a coil or a hypotube.

Embodiments of the method may include one or more of the following features: extending a second longitudinally extending hollow member relative to the second driver to converge legs of the second plurality of legs wherein the second longitudinally extending hollow member may comprise a coil or a hypotube, and wherein extending the first longitudinally extending hollow member and second longitudinally extending hollow member is performed independently of each other; retracting at least one of the first longitudinally extending hollow member relative to the first driver and the second longitudinally extending hollow member relative to the second driver; and releasing the object of interest.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Figure 1:
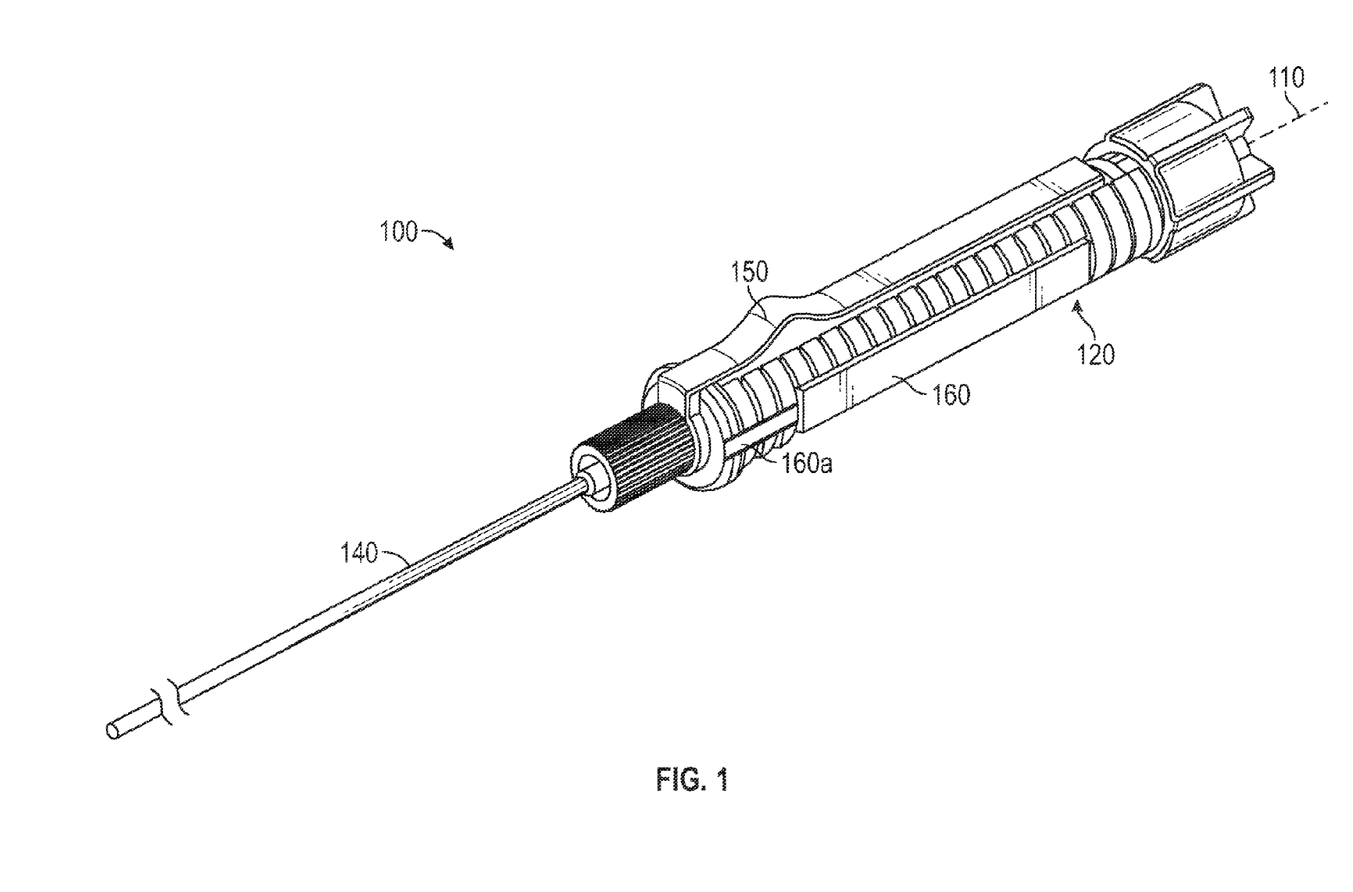
FIG. 1 illustrates an exemplary handle of a medical device according to an embodiment of the disclosure.

As shown in FIG. 1, a medical device 100 according to an exemplary embodiment of the present disclosure may include a handle 120 extending along a central longitudinal axis 110. Handle 120 may be configured to selectively extend and retract a medical retrieval device (e.g., a basket) 130 (not shown in FIG. 1) relative to a sheath 140, as will be described in further detail below. Accordingly, handle 120 may include an actuator 150 configured to reciprocally move basket 130 relative to sheath 140.

Actuator 150 may include, for example, a sliding mechanism, rotating mechanism, pushing mechanism, or the like. The actuator 150 may be coupled to drivers 260a and 260b (not shown in FIG. 1) in any conventional manner to control the movement of the basket 130. The drivers 260a and 260b may be a filament, braided or unbraided wire, rope, rod, or other suitable drive member having sufficient columnar strength to advance and retract basket 130 relative to a sheath 140. For example, upon actuation of actuator 150 in a first direction (e.g., distal direction), the drivers 260a and 260b may be configured to move the basket 130 between a collapsed position within sheath 140 and an expanded position distal of the sheath 140, as will be described in further detail below. It is understood that in some embodiments, a proximal end of drivers 260a and 260b may be coupled, joined, or otherwise secured together and connected to a wire, rod, and/or member (not shown) coupled to actuator 150. Accordingly, upon actuation of actuator 150 in a first direction (e.g., distal direction), the wire, rod, and/or member (not shown) may urge the drivers 260a and 260b to move the basket 130 between a collapsed position within sheath 140 and an expanded position distal of the sheath 140.

Handle 120 may include additional actuators 160 on respective sides of handle 120. While only a single actuator 160 is shown in FIG. 1, an additional actuator extends in mirror image to actuator 160 on the opposite side of handle 120. Actuators 160 may be configured to reciprocally move a respective one of hollow members 270a and 270b (see FIG. 2) relative to drivers 260a and 260b, as will be described in further detail below. For example, upon actuation of a first actuator 160 in a first direction (e.g., distal direction) along a slot 160a, hollow member 270a may move relative to and over driver 260a, and vice versa. Additionally, upon actuation of a second actuator 160 in a first direction (e.g., distal direction), hollow member 270b may move relative to and over driver 260b, and vice versa. In other embodiments, a single actuator 160 may be used to advance and retract hollow members 270a and 270b simultaneously. It is understood that while actuators 160 have been described as sliding mechanisms, additional or alterative mechanisms may be used such as, for example, a rotating mechanism, pushing mechanism, or the like.

Sheath 140 may include any appropriate polyimide tube or a hollow member of another material that exhibits suitable radial flexibility, axial stiffness, and biocompatibility. In addition, sheath 140 may have any appropriate outer dimension (e.g., diameter) and cross-sectional shape configured for insertion through a channel of a conventional insertion device such as, for example, a scope device (such as a ureteroscope, endoscope, colonoscope, etc.), a catheter, a sheath, or the like.

Figure 2:
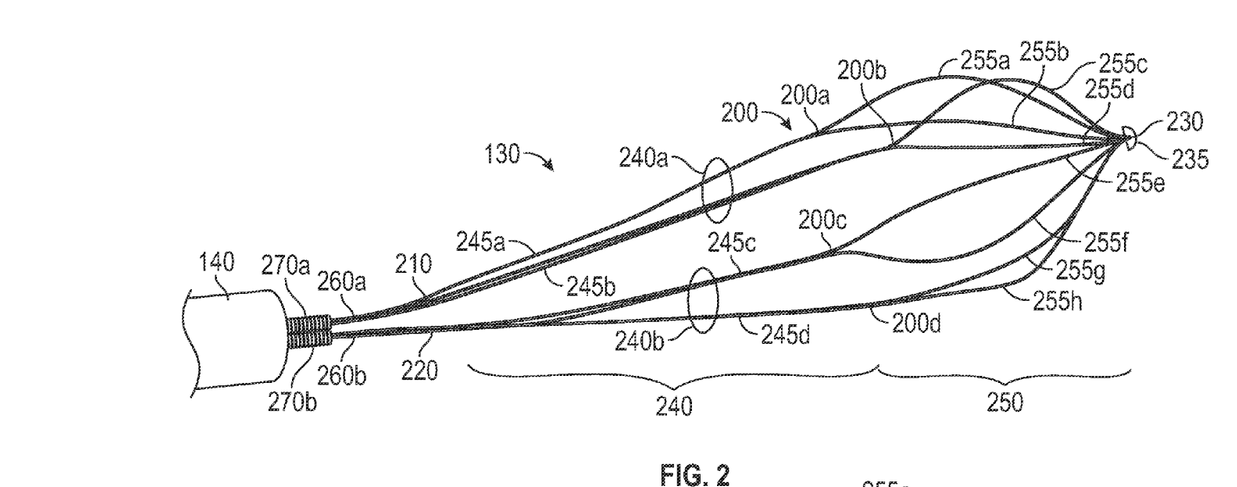
FIG. 2 illustrates an exemplary basket of an exemplary medical device according the an embodiment of the present disclosure.
Figure 3:
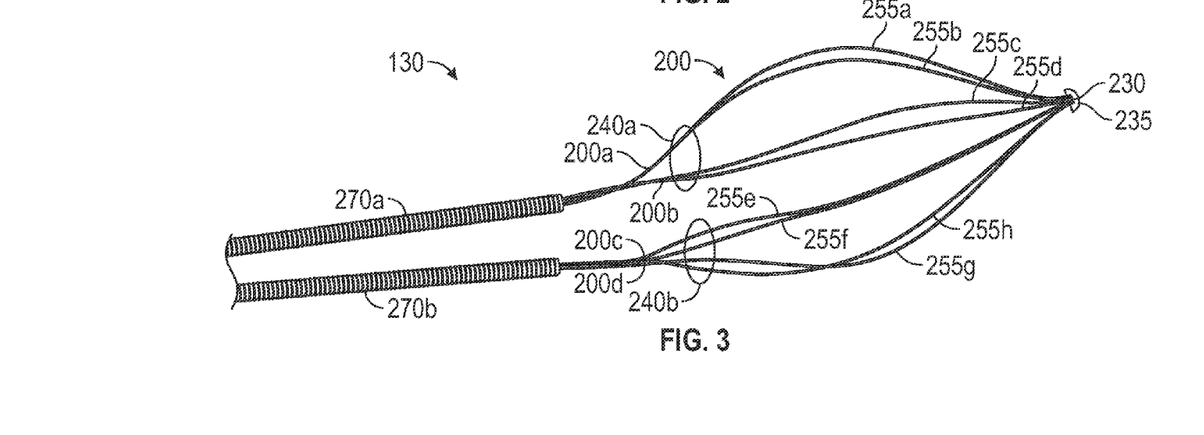
FIG. 3 illustrates a partially collapsed configuration of the basket of FIG. 2.

As shown in FIG. 2, basket 130 may comprise a plurality of interconnected legs or struts (e.g., wires) 200 extending from a first end 210 to a second end 220. A portion of the plurality of legs 200 between the first end 210 and the second end 220 may be coupled to form a basket tip 230. Basket tip 230 may be rounded atraumatic and/or include a rounded or atraumatic cap 235 on tip 230. Basket 130 may have any number of legs 200. The number of legs 200 may be selected on the basis of a number of parameters such as, for example, the size of the body lumen/cavity into which the basket 130 is inserted, the size of the stone or other material to be removed, the consistency of the stone or other material, the position of the stone or other material, and the location and/or orientation of the stone or other material within a patient.

The basket 130 may be constructed by joining multiple legs 200 together at such that a "cage" is formed. In accordance with embodiments of the present disclosure, a method of basket 130 formation involves starting with a hollow tube or cannula. For axial basket features (e.g., features extending substantially axially along a longitudinal axis of the underlying basket 130 structure) slots are cut lengthwise along the exterior of the cannula wall substantially parallel to the longitudinal axis of the cannula. For helical, spiral, or other features that are not solely axial in direction (e.g., features that extend at an angle with respect to a longitudinal axis of the tube), diagonal slots are cut with both an axial and a radial component. After cutting and cleaning, the resulting tubes are compressed lengthwise (e.g., expanded radially) to spread the legs 200 and manipulate the legs 200 into a desired shape. This shape is then annealed into the material to form a desired basket configuration. The slotting pattern can be formed according to a laser cutting process. Other machining processes are possible, such as chemical etching, EDM (Electrical Discharge Machining), and joining individual legs 200 together by welding or other attachment methods. In some embodiments, basket 130 may be formed from cutting or stamping the basket 130 from a single piece of material.

The basket 130 configuration according to embodiments of the present disclosure can be made at least partially of a shape-memory material. Shape-memory material is a material that can be formed into a particular shape, retain that shape during resting conditions (e.g., when the shaped material is not subject to external forces or when external forces applied to the shaped material are insufficient to substantially deform the shape), be deformed into a second shape when subjected to a sufficiently strong external force, and revert substantially back to the initial shape when external forces are no longer applied. Examples of shape memory materials include synthetic plastics, stainless steel, and superelastic metallic alloys of nickel/titanium (e.g., Nitinol), copper, cobalt, vanadium, chromium, iron, or the like. Alternative basket materials include, but are not limited to, other metal alloys, powdered metals, ceramics, thermal plastic composites, ceramic composites, and polymers. Also, combinations of these and other materials can be used.

As shown in FIG. 2, the basket 130 may include a proximal portion 240 and a distal portion 250. Each of the proximal portion 240 and distal portion 250 may include portions of legs 200, e.g., leg strands. The number of leg strands in the distal portion 250 may be greater than those in the proximal portion 240. Accordingly, the distal portion 250 may be configured to retain a stone or other material therein, thereby enabling a medical professional to retrieve and ultimately remove the stone from a patient. In other words, the distal portion 250 may act as a net for capturing and retrieving stones. As shown in FIG. 2, for example, the proximal portion includes four leg strands (245a-245d) while the distal portion includes eight leg strands (255a-255h). Such an arrangement, however, is merely exemplary, and each of the proximal portion 240 and distal portion 250 may include greater or fewer leg strands depending on the particular application. In addition, in some embodiments, the proximal portion 240 and the distal portion 250 may comprise equal numbers of leg strands.

Additionally, as shown in FIG. 2, the leg strands 245a-245b of the proximal portion 240 may be coupled to or monolithically formed with the leg strands 255a-255h of the distal portion 250. Accordingly, the basket 130 may include transition points 200a-200d. In one exemplary configuration, leg strand 245a may be coupled to or monolithically formed with leg strands 255a and 255b at point 200a. Additionally, leg strand 245b may be coupled to or monolithically formed with leg strands 255c and 255d at point 200b, leg strand 245c may be coupled to or monolithically formed with leg strands 255e and 255f at point 200c, leg strand 245d may be coupled to or monolithically formed with leg strands 255g and 255h at point 200d. In the embodiment shown, points 200a-200d are at the same axial position along the length of basket 130. In other embodiments, however, the points 200a-200d may be at different axial positions along the length of the basket 130.

As shown in FIG. 2, the leg strands 245a-245d in the proximal portion 240 are divided into two groups or bundles 240a and 240b. For example, of the four leg strands in the proximal portion 240 shown in FIG. 2, a first leg strand 245a and second leg strand 245b are gathered together to form bundle 240a, while a third leg strand 245c and fourth leg strand 245d are gathered together to form bundle 240b. In other embodiments, however, bundles 240a and 240b may comprise uneven numbers leg strands. In still further embodiments, including greater or fewer leg strands, bundles 240a and 240b may comprise more or less than two leg strands.

Each bundle 240a and 240b may be coupled to a driver 260a and 260b. For example, bundle 240a may be coupled to a driver 260a, and bundle 240b may be coupled to a driver 260b. It is understood, however, that only one single leg of each bundle 240a and 240b must be coupled to a respective driver 260a, 260b. Drivers 260a and 260b may be coupled to bundles 240a and 240b, respectively, through any conventional means such as welding, adhesive, or mechanical joints. Alternatively, drivers 260a and 260b may be monolithically formed with a respective one of bundles 240a and 240b such that drivers 260a and 260b are a one-piece continuous member with a respective one of bundles 240a and 240b.

The medical device 100 may further include two longitudinally extending hollow members 270a and 270b such as, for example, a coil and/or a hypotube or any other appropriate tubing, braided tubing, or other flexible tubing structure. Each hollow member 270a, 270b may extend from the handle 120, through the sheath 140, and to a distal end of the medical device 100. A proximal end of hollow member 270a may be operably coupled with a first actuator 160 while a proximal end of hollow member 270b may be operably coupled with a second actuator 160. Hollow member 270a may be configured to receive driver 260a therein, while hollow member 270b may be configured to receive driver 260b therein.

Hollow members 270a and 270b may further be configured to move relative to drivers 260a and 260b, respectively. In addition, hollow members 270a and 270b may include any appropriate biocompatible material, such as, for example, stainless steel, polymers, metals, etc. In some embodiments, an interior or exterior surface of hollow members 270a and/or 270b may comprise a lubricious coating configured to reduce friction and ease movement of hollow members 270a and 270b relative to drivers 260a and 260b and/or sheath 140.

Referring to FIGS. 1-4, a method of operating medical device 100 will be described. First, a medical professional may introduce medical device 100 into the body of a patient through any appropriate means such as, for example, a scope or similar introducer device. Once positioned, a medical professional may manipulate actuator 150 such that basket 130 extends distally of sheath 140 as shown in FIG. 2. Once basket 130 extends distally of the sheath 140, the basket 130 may expand to form a cage configured to capture and retrieve a stone or other material from within the body of the patient.

During use, a stone or other material may be captured within the basket 130. If, however, the stone or material is too large to be removed intact from the body tract after it has been captured within basket 130, a user may deploy two longitudinally extending hollow members 270a and 270b to release the oversized stone or material from the basket 130 via actuators 160. For example, a medical professional may urge first actuator 160 in a distal direction, thereby extending hollow member 270a distally. Additionally or alternatively, a medical professional may urge second actuator 160 in a distal direction, thereby extending hollow member 270b distally. Urging one or both of hollow members 270a, 270b distally results in hollow members 270a, 270b moving (e.g., sliding, translating) relative to and over legs 200 of the basket 130. For example, hollow member 270a may be urged over bundle 240a while hollow member 270b may be urged over bundle 240b.

Figure 4:
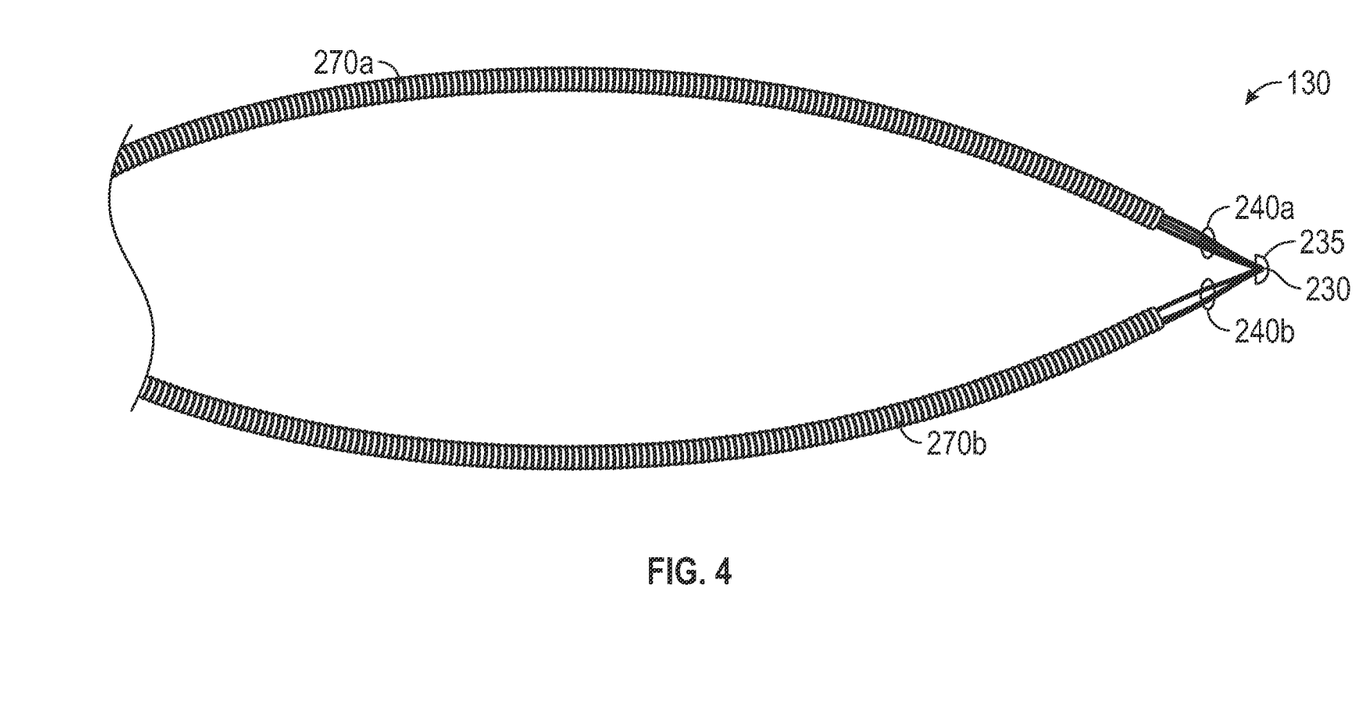
FIG. 4 illustrates a fully collapsed configuration of the basket of FIG. 2.

As shown in FIG. 4, continuing to advance hollow members 270a and 270b in a distal direction relative to bundles 240a and 240b may collapse the basket 130 such that an oversized stone or material may be released. For example, advancement of hollow member 270a towards basket tip 230 and advancement of hollow member 270b towards basket tip 230 may split the basket 130 such that bundles 240a and 240b are contained within the hollow members 270a and 270b and the basket 130 is prevented from expanding. That is, advancement of hollow member 270a may result in leg strands 245a and 245b converging towards one another, while advancement of hollow member 270b may result in leg strands 245c and 245d converging toward one another. Advancement of hollow member 270a distally of transition points 200a and 200b may further result in leg strands 255a-255d converging towards one another, while advancement of hollow member 270b distally of transition points 200c and 200d may further result in leg strands 255e-255h converging towards one another. Accordingly, once the hollow members 270a and 270b are extended toward the basket tip 230, the leg strands 245a-245d and 255a-255h are prevented from expanding relative to each other and the basket 130 no longer forms a cage. As such, an oversized stone or material is freely released. That is, as legs 245a and 245b converge, and as legs 245c and 245d converge, the space between legs 245b and 245c expands such that an oversized stone or other material may escape basket 130. Additionally, as legs 255a-d converge, and as legs 255e-h converge, the space between legs 255d and 255e expands such that an oversized stone or other material may escape basket 130. As shown in FIG. 4, flexible hollow members 270a and 270b may be configured to bend in an arcuate manner once extended distally of sheath 140. Once released, a medical professional may retract hollow members 270a and 270b via actuators 160 such that basket 130 may return to its expanded configuration (e.g., leg strands 245a-d and leg strands 255a-h are free to diverge and spread apart from one another). Accordingly, a medical professional may redirect the medical device 100 to capture a different stone and/or material within the body of a patient.

In other embodiments, the method may include introducing the medical device 100 into the body of a patient through any appropriate means such as, for example, a scope or similar introducer device. Once positioned, a medical professional may manipulate actuator 150 and actuators 160 such that basket 130 and hollow members 270a and 270b extends distally of sheath 140 as shown in FIG. 4. Next, a medical professional may manipulate the medical device such that it surrounds a stone or other material. Once positioned about the stone or material, a medical professional may retract hollow members 270a and 270b via actuators 160 such that the basket 130 may expand around the stone or material. If, however, the stone or material is too large to be removed intact from the body tract after it has been captured within basket 130, the medical professional may then extend hollow members 270a and 270b via actuators 160 as described above.

In other embodiments, an additional outer sheath (not shown) may be disposed externally of sheath 140 and the sheath 140 may be in a retracted configuration, as shown in FIG. 2. In use, a medical professional may introduce the medical device 100 into the body of a patient through any appropriate means such as, for example, a scope or similar introducer device. Once positioned, a medical professional may retract the outer sheath relative to the medical device 140 thereby allowing basket 130 to assume its expanded shape, as shown in FIG. 2. As such, the basket 130 may expand to form a cage configured to capture and retrieve a stone or other material from within the body of the patient.

In other embodiments, it is understood that hollow members 270a and 270b may be used to clean and/or wipe legs of basket 130. For example, during a procedure, basket 130 may become clogged with blood, tissue, or other material. Accordingly, one or both of hollow members 270a and 270b may be extended distally relative to legs of basket 130, as noted above, in order to wipe, scrape, or otherwise clean such material from the basket 130.

It is understood that in some embodiments, only one of hollow members 270a and 270b may be advanced to release an oversized stone or other material. Additionally, it is understood that while only two bundles 240a and 240b and two hollow members 270a and 270b are shown, embodiments of the present disclosure may include additional bundles 240 and hollow members 270.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the disclosure is not to be considered as limited by the foregoing description.

I claim:

1. A medical device, comprising:
a distal assembly including a first plurality of legs and a second plurality of legs, wherein the first plurality of legs and the second plurality of legs are joined at a distal tip;
a first driver and a second driver, wherein a proximal end of at least one leg of the first plurality of legs is coupled to the first driver, and a proximal end of at least one leg of the second plurality of legs is coupled to the second driver;
a first longitudinally extending hollow member movably positioned along the first driver; and
a second longitudinally extending hollow member movably positioned along the second driver;
wherein movement of the first longitudinally extending hollow member relative to the first driver converges legs of the first plurality of legs, and movement of the second longitudinally extending hollow member relative to the second driver converges legs of the second plurality of legs, wherein each of the first longitudinally extending hollow member and the second longitudinally extending hollow member is independently movable.

2. The medical device of claim 1, wherein each of the first plurality of legs and the second plurality of legs includes a proximal portion and a distal portion, wherein the distal portion includes more legs than the proximal portion.

3. The medical device of claim 2, wherein the proximal portion comprises four legs and the distal portion comprises eight legs.

4. The medical device of claim 2, wherein the proximal portion of the first plurality of legs comprises a different number of legs than the proximal portion of the second plurality of legs.

5. The medical device of claim 1, wherein each of the first longitudinally extending hollow member and the second longitudinally extending hollow member is configured to slide over a corresponding one of the first plurality of legs and the second plurality of legs.

6. The medical device of claim 1, wherein the first plurality of legs and the second plurality of legs are cut from a tube.

7. The medical device of claim 1, wherein each of the first longitudinally extending hollow member and the second longitudinally extending hollow member comprises a coil or a hypotube.

8. The medical device of claim 1, wherein each of the first longitudinally extending hollow member and the second longitudinally extending hollow member includes a lubricious coating.

9. The medical device of claim 1, further comprising:
a handle coupled to a sheath, wherein the handle includes an actuator configured to reciprocally move the first plurality of legs and the second plurality of legs from a position within the sheath to a position extending distally of the sheath, and a first hollow member actuator and a second hollow member actuator configured to reciprocally move the first longitudinally extending hollow member and the second longitudinally extending hollow member relative to the first driver and the second driver, respectively.

10. A method, comprising:
delivering a medical device to an area within a patient, the medical device comprising a first driver, a second driver, and a distal assembly, the distal assembly being configured to transition between a first retracted configuration within a sheath and a second deployed configuration extending distally of the sheath;
moving the distal assembly to the deployed configuration;
capturing an object of interest within the distal assembly, the distal assembly including a first plurality of legs, a second plurality of legs, and a distal tip wherein the first plurality of legs and the second plurality of legs are joined at the distal tip, wherein a proximal end of at least one leg of the first plurality of legs is coupled to the first driver, and a proximal end of at least one leg of the second plurality of legs is coupled to the second driver; and
extending a first longitudinally extending hollow member relative to the first driver and converging legs of the first plurality of legs, and extending a second longitudinally extending hollow member relative to the second driver and converging legs of the second plurality of legs, wherein each of the first longitudinally extending hollow member and the second longitudinally extending hollow member is independently movable.

11. The method of claim 10, further comprising:
releasing the object of interest.

12. The method of claim 10, further comprising:
retracting the first longitudinally extending hollow member relative to the first driver; and
retracting the second longitudinally extending hollow member relative to the second driver.

13. The method of claim 10, wherein extending the first longitudinally extending hollow member relative to the first driver and the second longitudinally extending hollow member relative to the second driver comprises extending the first longitudinally extending hollow member independently of the second longitudinally extending hollow member.

14. The method of claim 10, further comprising:
actuating a first hollow member actuator to extend the first longitudinally extending hollow member and actuating a second hollow member actuator to extend the second longitudinally extending hollow member.

15. The method of claim 10, wherein each of the first longitudinally extending hollow member and second longitudinally extending hollow member comprises a coil or a hypotube.

16. A method, comprising:
delivering a medical device to an area within a patient, the medical device comprising a first driver, a second driver, and a distal assembly, the distal assembly being configured to transition between a first retracted configuration within a sheath and a second deployed configuration extending distally of the sheath;
moving the distal assembly to the deployed configuration;
capturing an object of interest within the distal assembly, the distal assembly including a first plurality of legs, a second plurality of legs, and a distal tip wherein the first plurality of legs and the second plurality of legs are joined at the distal tip, wherein a proximal end of at least one leg of the first plurality of legs is coupled to the first driver, and a proximal end of at least one leg of the second plurality of legs is coupled to the second driver;
extending a first longitudinally extending hollow member relative to the first driver to converge legs of the first plurality of legs, wherein the first longitudinally extending hollow member comprises a coil or a hypotube; and extending a second longitudinally extending hollow member relative to the second driver to converge legs of the second plurality of legs, wherein the second longitudinally extending hollow member comprises a coil or a hypotube, and wherein extending the first longitudinally extending hollow member and the second longitudinally extending hollow member is performed independently of each other.

17. The method of claim 16, further comprising:
retracting at least one of the first longitudinally extending hollow member relative to the first driver and the second longitudinally extending hollow member relative to the second driver.

18. The method of claim 16, further comprising:
releasing the object of interest.

* * * * *